United States Patent [19]
Joulia

[11] Patent Number: 5,861,165
[45] Date of Patent: *Jan. 19, 1999

[54] MAKE-UP PRODUCT

[75] Inventor: Gérard Joulia, Paris, France

[73] Assignee: L'Oreal, Paris, France

[*] Notice: The term of this patent shall not extend beyond the expiration date of Pat. No. 5,798,110 and Pat. No. 5,702,713.

[21] Appl. No.: 904,861

[22] Filed: Aug. 1, 1997

Related U.S. Application Data

[63] Continuation of Ser. No. 601,648, Feb. 14, 1996, Pat. No. 5,702,713.

[30] Foreign Application Priority Data

Feb. 14, 1996 [FR] France .................................. 93-06763

[51] Int. Cl.⁶ .............................. A61K 7/00; A61K 7/021
[52] U.S. Cl. .............................. 424/401; 424/69; 424/63; 132/293
[58] Field of Search .............................. 424/407, 69, 63; 132/293

[56] References Cited

U.S. PATENT DOCUMENTS

| | | |
|---|---|---|
| 1,968,475 | 1/1934 | Beckwith . |
| 4,156,067 | 5/1979 | Gould . |
| 4,337,859 | 7/1982 | Murphy ..................................... 206/37 |
| 4,548,861 | 10/1985 | Barnes et al. . |
| 4,724,138 | 2/1988 | Duffy ..................................... 424/63 |
| 4,804,538 | 2/1989 | Chen . |
| 5,049,376 | 9/1991 | Murphy . |

FOREIGN PATENT DOCUMENTS

| | | |
|---|---|---|
| 0 191 198 | 8/1986 | European Pat. Off. . |
| 0 528 705 | 2/1993 | European Pat. Off. . |
| 1 520 770 | 3/1968 | France . |
| 2 519 580 | 7/1983 | France . |
| 16 29 523 | 2/1971 | Germany . |
| 61-112602 | 5/1986 | Japan . |

OTHER PUBLICATIONS

Hitachi, Database WPI, Week 8628, Derwent Publications, Ltd. Great Britain, AN 86–179569 & JP–A–61 112 602, May 30, 1986.

French Search Report dated Dec. 1993 in French Priority Application.

*Primary Examiner*—Sally Gardner-Lane
*Attorney, Agent, or Firm*—Staas & Halsey

[57] ABSTRACT

Process for moulding a make-up composition in a mould comprising a concave moulding surface forming the base of the mould and a bottom forming the upper component of the mould and closing off the space bounded by the said moulding surface, the composition being cast in the said mould in fluid form and subsequently solidifying to form a demouldable solid product capable of being packaged, in which the said composition is cast in a mould (1) whose bottom consists at least partly of a sheet (2) of open-cell plastic foam, so as partly to impregnate the said foam sheet (2) with the said composition and in which, after solidifying of the said composition, a moulded product consisting of the solidified composition and of the foam sheet which is bonded to it and which forms its support, is demoulded by removing the moulding surface (1).

16 Claims, 2 Drawing Sheets

FIG. 1a
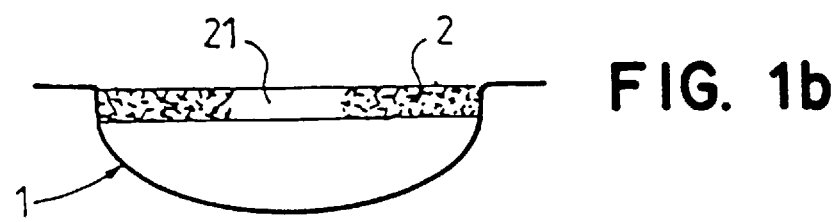
FIG. 1b
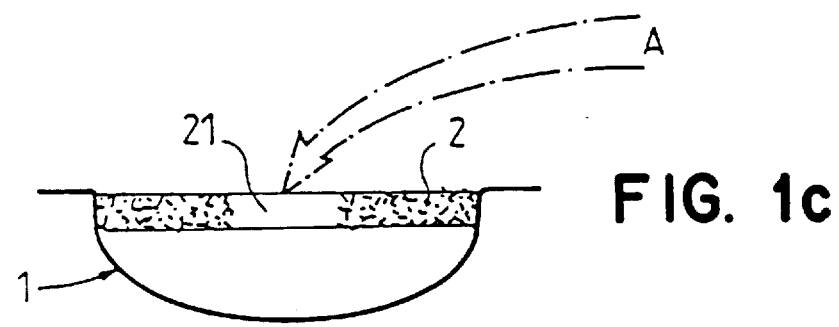
FIG. 1c
FIG. 1d
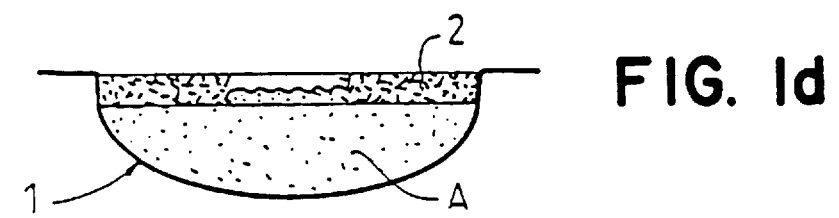
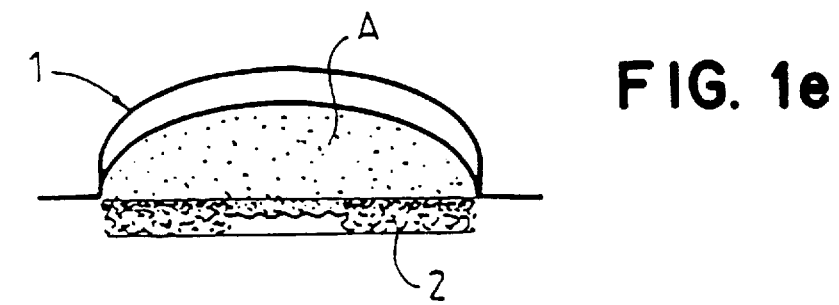
FIG. 1e
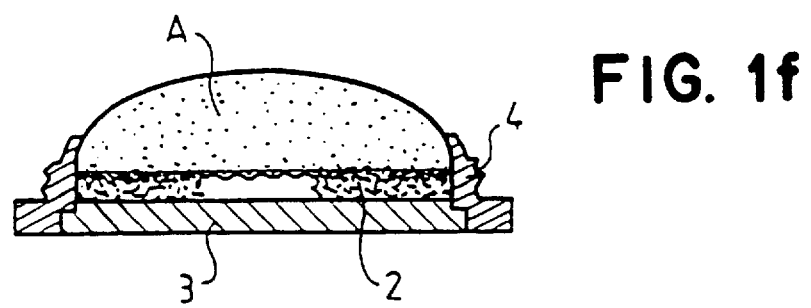
FIG. 1f

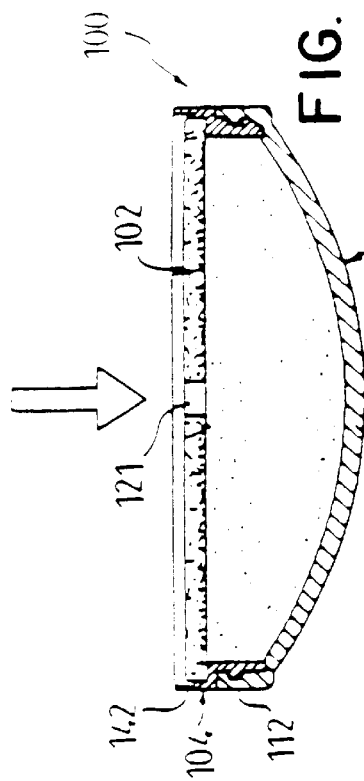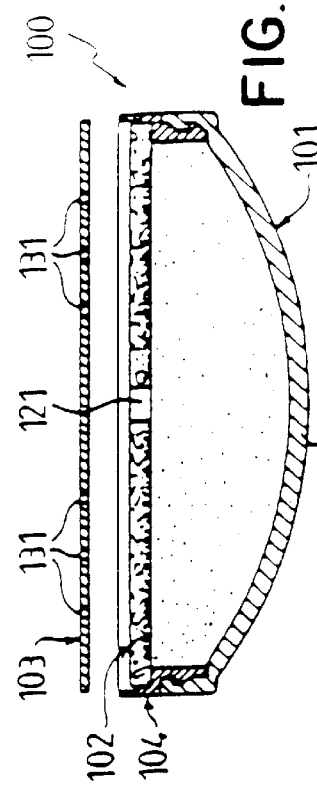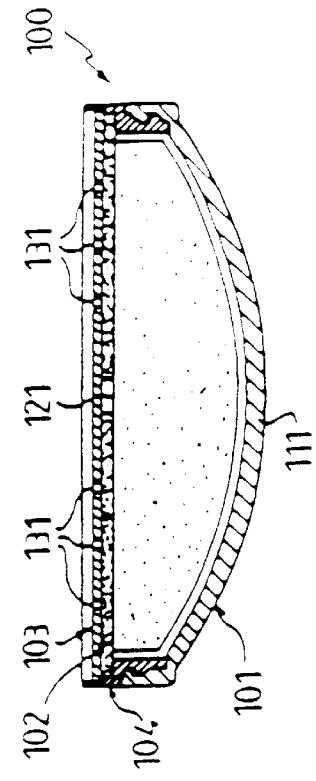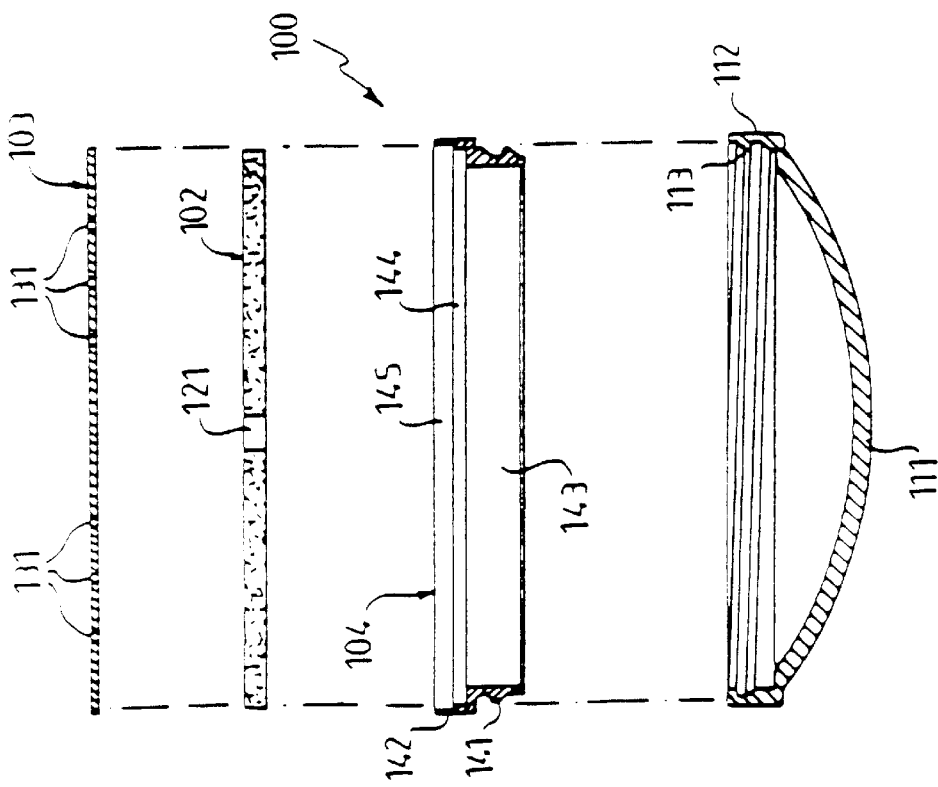

MAKE-UP PRODUCT

This application is a continuation, of application number 08/601,648, filed Feb. 14, 1996, now U.S. Pat. No. 5,702,713.

BACKGROUND OF THE INVENTION

The present invention relates to a process for molding a make-up composition by casting in a mold, in fluid form, and solidifying the composition, so as to obtain a solid molded product in the form of a block or cake, it being subsequently possible for the composition to be picked off from the molded product with the aid of a finger, a brush or a puff; the invention also relates to the product obtained by this process.

The make-up composition to be molded may be in the form of a paste obtained by mixing a solid particulate phase either with an aqueous phase or with a binding agent, especially a fatty phase, in a solvent; it may also be in the form of a product based on a heat-fusible wax or of a gel which is cast in the hot state. Depending on the composition employed, the solidification therefore takes place either by evaporation of water or of solvent, or by cooling, or by chemical reaction.

It is known to cast a make-up composition in a mold of a certain volume including chiefly a molding surface which imparts its shape (flat, curved or provided with relief or indented figures) to the surface for taking off the composition and a bottom, in most cases flat, provided with one or more openings through which the composition to be molded is cast. Depending on the make-up composition which is processed, the phenomenon of shrinkage during the solidification may be considerable. This is the case especially with the compositions described in patents U.S. Pat. No. 4,804,538, EP-A-165,137 and DE-A-3,327,001. The molded block obtained is then packaged but, because of the shrinkage, its dimensions and its shape can vary, and it is difficult to keep it in place in this package and to wedge it against the rigid surface forming the bottom of the package such as a case; the main function of the rigid surface is to prevent the molded block from breaking up in the course of the various handling operations and to protect it, but the shrinkage destroys the wedging and prevents the packaging from fulfilling its function in a satisfactory manner. If the molded block is badly wedged it tends to break up in the course of storage; because of its nature it is actually very brittle because it must be capable of being disintegrated to allow it to be picked off.

To avoid this disadvantage it has already been proposed, in EP-A-191,198 and in EP-A-38,645, to perform the casting in a dish resting on a molding surface, the bottom of the dish being provided with crosspieces, reinforcement or other anchoring devices. On solidifying, the composition binds to the bottom of the dish and a product of molding is then packaged, including of the solidified composition and its associated dish. The dish is used as a support for the solidified composition and, since the dish has determined dimensions, the molded product is easy to keep in place and to wedge in a rigid package. However, it has been found that after drying or cooling, cracks are formed because of a shrinkage of the composition in relation to the dish and to the regions for bonding to the latter. The product sold is consequently embrittled and tends to fragment during the various subsequent handling operations, especially when the product is being used.

It is therefore desirable to define a packaging for this type of composition, which at the same time makes it possible to ensure the wedging and the maintaining of the solidified composition in a protective packaging eliminating the risk of breaking up and to permit the shrinking of the composition without embrittlement of the molded block; two functions must therefore be ensured simultaneously.

SUMMARY OF THE INVENTION

According to the present invention it has been found that the abovementioned disadvantages are avoided by employing a mold bottom including a sheet of open-cell foam which is partly impregnated with the cast composition. The process according to the invention makes it possible to ensure the two desirable functions defined above simultaneously with the product obtained.

The subject of the present invention is therefore a process for molding a make-up composition in a mold including a concave molding surface forming the base of the mold and a bottom forming an upper component of the mold and shutting off a space bounded by the molding surface, the composition being cast in the mold in fluid form and subsequently solidifying to form a demoldable solid product capable of being packaged. The composition is cast in a mold the bottom of which is at least partly formed by a sheet of open-cell plastic foam, so as partly to impregnate the foam sheet with the composition. After solidification of the composition a molded product, including the solidified composition and the foam sheet which is bonded to it and which forms its support, is demolded by removing the molding surface.

It has been found that, in the process according to the invention, compositions exhibiting a high shrinkage during their solidification can be cast without the molded product obtained being fragile because the foam support adapts its shape to the dimensional changes in the solidified composition by virtue of its elasticity. Nevertheless, since the foam is partly impregnated with the composition, a bond is formed between the plastic foam sheet and the composition during the solidification and the foam sheet forms a support for the solidified composition, a support which, of itself, contributes to the mechanical reinforcement of the molded block. A molded product is therefore prepared, including the combination of the solidified composition and the foam sheet. The unimpregnated portion of the foam sheet, more particularly the unimpregnated layer of the foam sheet, which has retained its elasticity, can be employed in the packaging of the molded product to wedge the latter onto a rigid surface by compensating the changes in dimensions of the solidified composition; the wedging is produced by a slight compression of the foam sheet. In addition, the solidified composition, being held in the package on an elastic surface, is properly protected against the impacts to which it might be subjected during the various handling operations. A good conservation of the molded product is therefore ensured as soon as it is manufactured, until it reaches the user's hands.

According to a first embodiment the composition is solidified after casting by cooling or by evaporation of a solvent present in the composition. According to another embodiment a composition which contains plaster ($CaSO_4 \cdot \frac{1}{2}H_2O$) and a sufficient quantity of water to obtain a pourable mixture is cast, the solidification taking place after casting by setting of the plaster. The molding process according to the invention is then particularly advantageous.

According to the invention the composition may be cast through the foam sheet; casting takes place preferably through an opening, advantageously a central opening, made in the foam sheet. The size of this opening is a function of the size of the mold and of the composition which is cast.

The foam sheet is preferably slightly compressed at the solidification stage, advantageously with the aid of a rigid plate; this rigid plate is advantageously provided with openings to facilitate the evaporation when the solidification takes place by evaporation.

The foam sheet employed according to the invention includes, as indicated above, an open-cell plastic foam. This foam is chosen so that it practically does not swell in the presence of the various ingredients of the make-up composition, such as water, oil and fatty substances, and so that it can be impregnated with the composition. A foam is advantageously employed which has a cell structure such that the volume occupied by the walls of the cells does not represent more than 3% of the total volume of the foam. The foam advantageously has a homogeneous cell structure, that is to say forming a three-dimensional network. Suitable plastic foams are, for example, crosslinked polyurethane foams, in particular those marketed under the names "Bulpren S 20", "Bulpren S 30" and "Filtren S 2120" by the "Recticel" company.

The thickness of the foam sheet employed is a function of the size of the mold and of the composition which is cast. A suitable thickness is generally of the order of 3 to 6 mm.

Another subject of the present invention is the molded make-up product obtained by the process defined above.

This product is preferably packaged, after demolding, in a rigid display case including a component which supports the foam sheet and of a ring which surrounds the molded product and is integrally attached to the component.

In a first alternative form the component is a base which interacts with a ring which bears on the solidified composition to hold the molded product against the base, the said base overlapping laterally in relation to the foam sheet.

In a second alternative form the component is a plate and the ring includes a means of integral fastening capable of ensuring peripherally, in a removable manner, its bonding to a cap in order to form a molding surface with it. In addition, the plate preferably includes at least one opening.

Provision can be advantageously made for the product according to the invention to contain hydrated plaster ($CaSO_4 \cdot 2H_2O$), preferably in a proportion by weight of between 10 and 50%.

BRIEF DESCRIPTION OF THE DRAWINGS

The description given below, purely by way of illustration and without any limitation being implied, will make it possible to understand the invention better, reference being made to the attached drawings.

In this drawing:

FIG. 1 is a diagram of the various stages (a to f) of a first alternative form of the molding process according to the invention;

FIG. 2 shows an exploded view of a mold employed according to a second alternative form of the process according to the invention; and FIG. 3 shows the various stages of use of the mold illustrated in FIG. 2.

DESCRIPTION OF THE PREFERRED EMBODIMENTS

In the scheme shown in FIG. 1:

in stage a, a thermoformed dish 1, which forms a concave molding surface for the make-up composition is placed in position;

in stage b, a foam sheet 2 provided with a central opening 21 is placed in position in the the dish 1, this foam sheet 2 forming the bottom of the mold;

in stage c, a cosmetic composition A is poured in through the opening 21, as shown by the arrow, and the mold is completely filled so as to impregnate the lower layer of the foam sheet 2 with composition A while leaving free the upper layer of the foam sheet, this upper layer consequently retaining its elasticity;

in stage d, the composition A is allowed to solidify; a mechanical bond is then formed between the foam sheet 2 and the solidified composition A;

in stage e, the molded product, including a curved tablet of solidified composition A and of the foam sheet 2 which forms its support, is removed from the mold stage f is the stage of packaging of the molded product; the molded product is held down on a rigid base 3 with the aid of a ring 4 while the foam sheet 2 is slightly compressed; the ring 4 bears on the tablet of composition A and the base 3 is integrally attached to the ring 4 to keep the foam compressed. In this way, by virtue of its elasticity, the foam sheet 2 makes it possible to compensate, in relation to the base 3 and the ring 4, the deformations of the solidified tablet of composition A which are due to shrinkage during and after solidification. The tablet of composition A is therefore well supported and well wedged on the rigid base 3 without any risk of cracking of the solidified composition.

FIG. 2 shows an exploded view of the various parts forming a mold 100 for making use of a second alternative form of the process according to the invention, an alternative form which is preferred because it makes it possible to mold the molded product directly in the packaging. It is made up, firstly, of a molding surface in the form of a dish referred to as 101 as a whole, as can be seen in FIG. 3A, secondly of a foam sheet 102 in the form of a circular disc and, thirdly, of a rigid plate 103 also in the form of a circular disc, of the same area as that of the foam sheet 102.

The molding surface 101 is made up, firstly, of a concave cap 111 on the edge of which is formed a cylindrical skirt 112 provided with an internal screw thread 113 and, secondly, with a removable ring 104 provided with an external screw thread 141 and capable of being fitted by screwing onto the skirt 112. The screw thread 141 is situated slightly set back from a cylindrical surface 142 which extends the external surface of the skirt 112 when the ring 104 is screwed onto the cap 111.

The inner surface of the ring 104 defines three zones of increasing diameter which are separated by shoulders: a zone of smallest diameter 143 which is situated on the side of the concave part of the cap 111 when the ring 104 is screwed onto the cap, a zone of larger diameter 144 which, allowing for the necessary clearance, is equal to the external diameter of the foam sheet 102 and a height which is lower than the thickness of the foam sheet 102 and, finally, a zone 145 of still larger diameter and of height which is close to the thickness of the rigid plate 103. The foam sheet 102 is provided with a central opening 121 and the rigid plate 103 is provided with several openings 131.

As illustrated in FIG. 3A, the ring 104 is fitted onto the cap 111, the foam sheet 102 is arranged in the zone 144 of the ring 104 screwed onto the skirt 112 of the cap 111, to form the molding surface 101. The cosmetic composition is introduced through the central opening 121 in the foam sheet 102 until the cosmetic composition fills the zone 144 of the ring and impregnates the foam over a proportion of its thickness—generally half its thickness; a bond between the solidified composition and the foam sheet 102 is thus obtained after solidifying. The plate 103 is then fitted by pressure in the zone 145 of the ring 104, slightly crushing the foam sheet 102 (see FIGS. 3B and 3C) on the shoulder between the zones 144 and 145 and thus ensures that the foam sheet is secured to the cast composition. This crushing can be performed before solidification is complete, in which case it takes part in the partial impregnation of the foam sheet 102, or after solidification is complete.

The cosmetic composition is then allowed to dry. The cells in the foam and the openings 131 arranged in the sheet 103 permit the evaporation of the solvent when the cosmetic composition solidifies by evaporation and, consequently, final drying.

After drying, the cap 111 is parted from the ring 104 and a unit 103, 102, 104 is thus obtained which can be marketed directly; the marketing may also take place with the cap 111 which then serves as a lid for protecting the composition.

The solidified cosmetic composition is held on the plate 103 by virtue of the foam sheet 102 trapped between the ring 104 and the plate 103. The stiffness of the plate 103 prevents any risk of breaking of the block forming the solidified composition. Nevertheless, the solidified composition can undergo shrinkage without cracking as a result of the elasticity of the foam sheet 102.

It suffices for the user to unscrew the molding surface 101 to release the surface for picking off the molded make-up composition and to pick off the make-up composition with the aid of a brush or of a puff.

Two examples of application of the process according to the invention are given below (the quantities are shown in g).

EXAMPLE 1

Preparation of an eye shadow

A paste which has the following formulation is prepared:
Phase A
- Talc . . . 9.7
- Chromium oxide . . . 1.8
- Ultramarine blue . . . 0.7
- Zinc stearate . . . 0.7
- Mica . . . 5.3
- Starch . . . 1.7
- Titanium mica . . . 10.5
- Hollow (single cavity) microspheres made of vinylidene chloride-acrylonitrile copolymer (density 0.02 g/cm$^3$) marketed under the name "Expancel 551 DE" by the company "Kemanord Plast". . . 1.4

Phase B
- Polyvinylpyrrolidone-hexadecene copolymer . . . 0.2
- Jojoba oil . . . 0.5
- Isopropyl myristate . . . 0.7
- Lanolin . . . 0.4
- Sweet almond oil . . . 1.2

Preserving agents
- Butylhydroxytoluene . . . 0.015
- Butylhydroxyanisole . . . 0.015
- Propyl para-hydroxybenzoate . . . 0.1

Solvent
- Cyclomethicone . . . 65

In a first step the constituents of phase B are mixed with each other. The constituents of phase A are introduced, separately, into a mixer, followed by the solvent and the whole is homogenized. Then, phase B into which the preserving agents have been introduced, is in turn introduced into the mixer and mixing is again carried out until a homogeneous paste is obtained.

The paste obtained is cast, at ambient temperature, in the concave mold 1 shown in FIG. 1. This mold is made of injection-molded polypropylene and is 60 mm in diameter and 20 mm in height. The bottom includes of a "Bulpren S 20" foam sheet 2 which is 6 mm in thickness and has a central opening 21, 15 mm in diameter; the paste is introduced through the central opening 21. The molds are then placed in an oven at 40° C. for 55 hours. A product including of the solidified composition integrally attached to the foam sheet 2 is then demolded; the demolded product is then held down on the rigid base 3, of the same size as the foam sheet 2, with the aid of the ring 4, so as to leave free the surface for picking off. A lid can then be fitted onto the ring 4 or the whole (solidified composition bonded to the foam sheet 2, ring 4 and base 3) can be introduced into a case.

The curved tablet of green-blue eye shadow which is obtained has a smooth and uniform surface which can be a picked off easily with a finger or with a brush.

EXAMPLE 2

Blusher

A pulverulent mixture which has the following formulation is prepared:
- Plaster (CaSO$_4$·½H$_2$O) . . . 25
- Talc . . . 25
- Talc coated with lauroyllysine, marketed under the name "EP 90025 Talc Treated" by the company "Mearl". . . 10
- Hollow (single cavity) microspheres of vinylidene chloride-acrylonitrile copolymer (density 0.02 g/cm$^3$), marketed under the name "Expancel 551 DE" by the company "Kemanord Plast". . . 5
- Mica . . . 24
- Calcium carbonate . . . 5
- Titanium dioxide . . . 2
- Red iron oxide . . . 3.5
- Black iron oxide . . . 0.5 and an aqueous phase which has the following composition:
- Water . . . 120
- Surfactant marketed under the name "Glucquat 100" by the company "Amerchol". . . 4.5
- Preserving agent . . . 0.1

The pulverulent mixture and the aqueous phase are mixed in a mixer equipped with slow stirring for 5 minutes.

The mixture obtained is introduced into the mold shown in FIG. 2; this mold is identical in dimensions with the mold in Example 1. The molding 101 uses, in combination with the concave cap 111 a ring 104 including three zones 143, 144, 145, which have the following heights: 7, 2, 2.5 mm, and the following diameters: 66, 70, 71.5 mm, respectively.

A disc of a foam 102 sold under the trade name "Filtren S 2120" 3 mm in thickness and which has a central circular opening 121 20 mm in diameter is introduced by pressure into the zone 144. The fluid composition is poured in through the opening 121. A foam thickness of approximately 1.5 mm is impregnated with solution. Approximately 30 minutes after the mold is filled, a plate 103 which, allowing for the necessary clearance, has the same diameter as the zone 145, is introduced by pressure into the ring 104, and this compresses the foam layer on the shoulder between the zones 143 and 144 over 2 mm and secures the foam sheet onto the plate 103. The plate comprises 24 uniformly distributed holes 1 mm in diameter to permit the final drying. The mold containing the solidified product is stored as is for approximately three days, and this allows the composition to dry because water vapor can escape through the openings 131 in the plate 103. The product is then marketed as is. It suffices for the user to unscrew the cap 111 to release the surface for picking off and to pick off the make-up composition with the aid of a puff or of a brush.

I claim:

1. A molded make-up product, comprising:

a solidified make-up composition having a first useable convex surface and a second, substantially flat opposite surface; and a foam sheet having open cells, wherein open cells of a first portion of the foam sheet are impregnated with the solidified make-up composition and are bonded thereby to the second, opposite surface of the solidified make-up composition, and a second, opposite portion which flexibly supports the solidified composition, wherein the make-up product has, as outer surfaces, the first useable surface from which make-up can be removed, and the second portion of the foam sheet.

2. Product according to claim 1, wherein the composition contains hydrated plaster ($CaSO_4 \cdot 2H_2O$).

3. Product according to claim 2, wherein the composition contains from 10 to 50% by weight of hydrated plaster.

4. Product according to claim 1, further comprising a case receiving the solidified composition and foam sheet.

5. Product according to claim 4, wherein the case includes a component which supports the second portion of the foam sheet, and a ring which surrounds the solidified composition and is attached to the component.

6. Product according to claim 4, wherein the component is a base which interacts with the ring to hold the product against the base, the base overlapping laterally in relation to the foam sheet.

7. Product according to claim 5, wherein the component is a plate and the ring includes a fastener capable of ensuring peripherally, in a removable manner, connection of the ring to a cap to form a molding surface therewith.

8. Product according to claim 7, wherein the plate comprises at least one opening.

9. The product according to claim 1, wherein the composition includes plaster.

10. The product according to claim 1, wherein the foam sheet includes an opening formed therein.

11. The product according to claim 1, further comprising a rigid plate attached to the second portion of the foam sheet.

12. The product according to claim 11, further comprising a ring attached to the rigid plate and abutting the composition and foam sheet.

13. Product according to claim 11, wherein the rigid plate includes at least one opening.

14. The product according to claim 1, wherein the foam sheet has a cell structure such that a volume occupied by walls of the cells does not represent more than 3% of a total volume of the foam.

15. The product according to claim 1, wherein the foam sheet is a crosslinked polyurethane foam.

16. The product according to claim 1, wherein the foam has a thickness of between 3 and 6 mm.

* * * * *